United States Patent
Willing et al.

(10) Patent No.: US 7,180,595 B2
(45) Date of Patent: Feb. 20, 2007

(54) GAS DETECTION METHOD AND GAS DETECTOR DEVICE

(75) Inventors: Bert Willing, Blonay (CH); Markus Kohli, Grandson (CH); Andreas Seifert, Denens (CH)

(73) Assignee: IR Microsystems AG, Lausanne (CH)

( * ) Notice: Subject to any disclaimer, the term of this patent is extended or adjusted under 35 U.S.C. 154(b) by 0 days.

(21) Appl. No.: 10/533,278

(22) PCT Filed: Jul. 30, 2004

(86) PCT No.: PCT/EP2004/008584

§ 371 (c)(1),
(2), (4) Date: Oct. 26, 2005

(87) PCT Pub. No.: WO2005/026705

PCT Pub. Date: Mar. 24, 2005

(65) Prior Publication Data

US 2006/0098202 A1     May 11, 2006

Related U.S. Application Data

(60) Provisional application No. 60/502,282, filed on Sep. 12, 2003.

(51) Int. Cl.
*G01N 21/61*     (2006.01)
*G01N 21/35*     (2006.01)

(52) U.S. Cl. .................. 356/437; 356/433; 250/339.11

(58) Field of Classification Search ........ 356/432–439; 250/573, 339.1, 339.11, 338.5, 458.1, 343
See application file for complete search history.

(56) References Cited

U.S. PATENT DOCUMENTS 4,059,356 A * 11/1977 Kebabian .................... 356/435

(Continued)

FOREIGN PATENT DOCUMENTS

JP     2001074654     3/2001

*Primary Examiner*—Sang H. Nguyen
(74) *Attorney, Agent, or Firm*—Bachman & LaPointe, P.C.

(57) ABSTRACT

A gas detector device comprises at least a VCSEL source (34, 36) and at least a light sensor (54, 56) for detecting a light beam (50, 52) having passed through a sample chamber (48) containing a given gas to be detected. The sensor is a photodiode in a first embodiment and its detection signal is time derivated by an electronic derivator (64) and then provided to two lock-in amplifiers (84, 86) in order to generate a F-detection and a 2F-detection, F being the frequency of a wavelength modulation of the source, and thus to provide two corresponding measuring signals the division of which gives a precise value of the gas concentration. In a second embodiment, the source is a pyroelectric sensor which directly provides a detection signal proportional to the time derivate of the light beam incident on this sensor. In this last case, the electronic derivator is thus eliminated.

4 Claims, 6 Drawing Sheets

U.S. PATENT DOCUMENTS

| | | | |
|---|---|---|---|
| 4,163,899 A * | 8/1979 | Burough .................. 250/343 |
| 5,173,749 A * | 12/1992 | Tell et al. .................. 356/437 |
| 5,332,901 A * | 7/1994 | Eckles et al. ............... 250/345 |
| 6,008,928 A * | 12/1999 | Sachse et al. ............... 359/246 |
| 6,064,488 A | 5/2000 | Brand et al. |
| 6,172,759 B1 | 1/2001 | Goldstein |
| 6,351,309 B1 * | 2/2002 | Bomse et al. ............... 356/437 |
| 6,356,350 B1 | 3/2002 | Silver et al. |
| 6,940,599 B1 * | 9/2005 | Hovde ....................... 356/432 |
| 6,995,846 B2 * | 2/2006 | Kalayeh et al. ............. 356/437 |
| 7,102,751 B2 * | 9/2006 | Harper ....................... 356/437 |
| 2003/0081875 A1 | 5/2003 | Kochergin et al. |

* cited by examiner

GAS DETECTION METHOD AND GAS DETECTOR DEVICE

This application is claimed Priority from Provisional Application of 60/502,282 filed on Sep. 12, 2003.

BACKGROUND OF THE INVENTION

The present invention concerns in particular low-cost infrared (IR) gas detection. A standard technology in this field consists in a thermal IR light source, an interference line filter, a sample chamber and an IR detector. The line filter corresponds to the characteristic absorption wavelength of the gas to be detected so that only light of this specific wavelength is incident onto the detector. If a gas to be detected is present in the sample chamber, part of the light is absorbed by the gas and the detector signal is lowered subsequently. In order to take into account the intensity variation of the light source due to aging, moisture or dirt, a part of the emitted light is directed outside the sample chamber onto a reference detector (so-called two-beam or reference-beam technique).

Such non-diffractive IR (NDIR) gas detectors suffer from two drawbacks. Firstly, thermal light sources have a high power consumption and a low light efficiency which makes battery-driven operation difficult and implies cooling issues. Secondly, the center wavelength of interference line filters is dependent on the temperature so that for different ambient temperatures, the detection operates at different positions of the gas absorption peak which in turn makes calibration difficult.

Recent developments with Vertical Cavity Surface Emitting Lasers (VCSEL) have shown a way to improve low-cost single gas detectors. VCSEL wavelengths are precisely defined and can be tuned over a few nanometers by a change of the VCSEL drive current. Such VCSEL diodes are meanwhile available for the near infrared (NIR) wavelength range of 1.3–2.05 µm. Many of the gases detected by IR absorption have the first or second overtones of their absorption peaks in this wavelength range. Although these overtones are substantially weaker than the fundamental peaks, gas detection is very sensitive as VCSELs typically supply about 1000 times more light intensity than a thermal light source. An important advantage of VCSELs is their low power consumption of a few Milliwatt compared to a few Watt for thermal light sources.

A main difference between a standard NDIR detection and detection based on VCSELs is that NDIR techniques have a low spectral resolution and therefore measure gas absorption peaks which are typically several 100 nm wide. These broad absorption peaks are in fact composed of a large number of very sharp absorption lines. VCSELs emit with a very sharp wavelength peak which can be modulated within a few nanometers. For this reason, a VCSEL-based gas detector measures one single absorption line instead of a broad absorption peak.

Several authors have described a gas detection set up with a VCSEL source where the wavelength of the VCSEL is scanned across the absorption line of the gas as represented in FIG. 2. This scanning is done with a given modulation frequency F. This modulation is achieved by imposing a small alternating current (100 µA typically) of frequency F onto a constant current above the lasing threshold (some mA typically). For some measurement techniques, this "constant current" is slowly swept across the whole operation range of the VCSEL in order to detect subsequent absorption lines. With such a set up, a line filter is no longer needed which is an important cost reduction factor for low-cost products.

The present invention is based on a source formed by a wavelength modulated VCSEL and uses the fact that the modulation of the wavelength is directly connected to a modulation of the VCSEL output intensity. The intensity of the light having passed the gas volume and being incident on the detector therefore shows a first modulation related to the VCSEL intensity and a second modulation related to the gas absorption as the wavelength is scanned across the gas absorption line.

With a standard IR detector which delivers a signal proportional to the incident radiation, the signal treatment consists in measuring the detector signal by a lock-in technique on twice the modulation frequency (2F-detection). By this, the DC signal component—which stems from the offset light detected throughout the modulation range—is suppressed. However, a reference beam has still to be used in order to obtain information about the overall light intensity of the initial light beam provided by the source for obtaining a precise value of the gas concentration. This reference beam is usually detected by a second specific detector. Thus, the generation and the detection of a reference beam complicate the device and increase its production cost.

U.S. Pat. No. 6,356,350 B1 describes a method and an apparatus for demodulating a plurality of frequency components output from a photodetector in a wavelength modulation spectroscopy system and determining absorption line shapes from the demodulated data. The method allows information about the absorber line shape and line width, gas concentration measurement over a range of gas pressures temperatures and concentrations. For this, at least two even harmonics or a plurality of an harmonics of the wavelength modulation frequency F are necessary. In general, the prior art document teaches to use more even harmonic demodulated frequency components than other frequency components. The method disclosed in U.S. Pat. No. 6,356,350 B1 is not appropriate for providing a gas detector device with low fabrication costs for large series which allows an efficient gas concentration measuring or presence of a gas.

An object of the present invention is to provide an efficient gas concentration measuring device or detector at low cost. In particular, the aim of the present invention is to solve the above mentioned problem relative to the reference beam.

SUMMARY OF THE INVENTION

Therefore, a first embodiment of the present invention concerns a gas detector device comprising a wavelength modulated laser source and a light sensor respectively arranged at the periphery of a detection region intended for receiving at least a gas the concentration of which is to be determined, said source providing an initial light signal which is wavelength modulated at a given frequency around an absorption line of said gas, said light sensor receiving a resulting light signal formed by the initial light signal having passed through said detection region, wherein the light sensor is of the type providing a detection signal substantially proportional to the time derivate of said resulting light signal thus forming an electronic signal which is substantially proportional to the time derivate of said resulting light signal, said device further comprising first means for generating a first modulation reference signal at said given frequency and second means for generating a second modulation reference signal at twice this frequency, said electronic signal being multiplied by said first modulation reference signal and then integrated over time in order to provide a first measuring signal which is a function of the intensity of said initial light signal and substantially independent of the concentration of said gas, said electronic signal being also multiplied by said second modulation reference signal and then integrated over time in order to provide a second measuring signal which is a function of the gas absorption and substantially independent of an intensity modulation of said initial light signal at said given first frequency.

Further, a second embodiment of the present invention concerns a gas detector device comprising a wavelength modulated laser source and a light sensor respectively arranged at the periphery of a detection region intended for receiving at least a gas the concentration of which is to be determined, said source providing an initial light signal which is wavelength modulated at a given frequency around an absorption line of said gas, said light sensor receiving a resulting light signal formed by the initial light signal having passed through said detection region, wherein the light sensor is of the type providing a detection signal proportional to said resulting light signal, the device further comprising an electronic time derivator to which the detection signal is provided, this electronic time derivator generating an electronic signal which is substantially proportional to the time derivate of said resulting light signal, said device further comprising first means for generating a first modulation reference signal at said given frequency and second means for generating a second modulation reference signal at twice this frequency, said electronic signal being multiplied by said first modulation reference signal and then integrated over time in order to provide a first measuring signal which is a function of the intensity of said initial light signal and substantially independent of the concentration of said gas, said electronic signal being also multiplied by said second modulation reference signal and then integrated over time in order to provide a second measuring signal which is a function of the gas absorption and substantially independent of an intensity modulation of said initial light signal at said given frequency.

Owing to the features of the gas detector device of the invention, only a single sensor unit is needed for one laser source, all necessary information for determining a precise gas concentration value being given by the processing of the generated electronic signal which is proportional to the derivate of the light signal received by the sensor unit after having passed through a sample of the defined gas.

BRIEF DESCRIPTION OF THE DRAWINGS

Other particular features and advantages of the present invention will be described with reference to the following description and the annexed drawings, given by way of non limiting embodiments, in which.

DETAILED DESCRIPTION

With reference to FIGS. 1 to 9, the method for detecting a gas concentration according to the present invention will be described.

Figure 1:
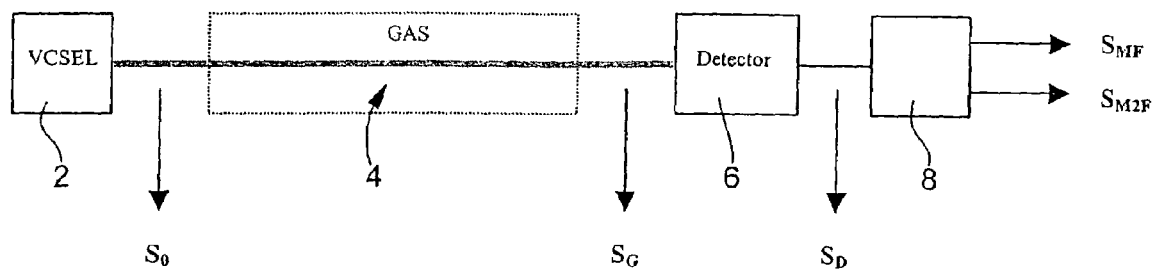
FIG. 1 shows schematically a gas detector device according to the present invention.

As schematically shown in FIG. 1, the gas detector device according to the invention comprises a light source formed by a VCSEL 2, a sample chamber or detection region 4 where a gas to be detected can be introduced, a light detector 6 and processing means 8 which provide two measuring signal $S_{MF}$ and $S_{M2F}$ allowing a gas concentration to be defined. The VCSEL generates an initial light beam $S_0$ which is wavelength modulated. This light beam passes through the region 4. Due to the gas absorption, the initial light signal presents an intensity variation after having passed through the gas detection region 4 and thus the detector 6 receives a resulting light signal $S_G$. The detector provides a corresponding detection signal $S_D$ to the processing means 8.

Figure 2:
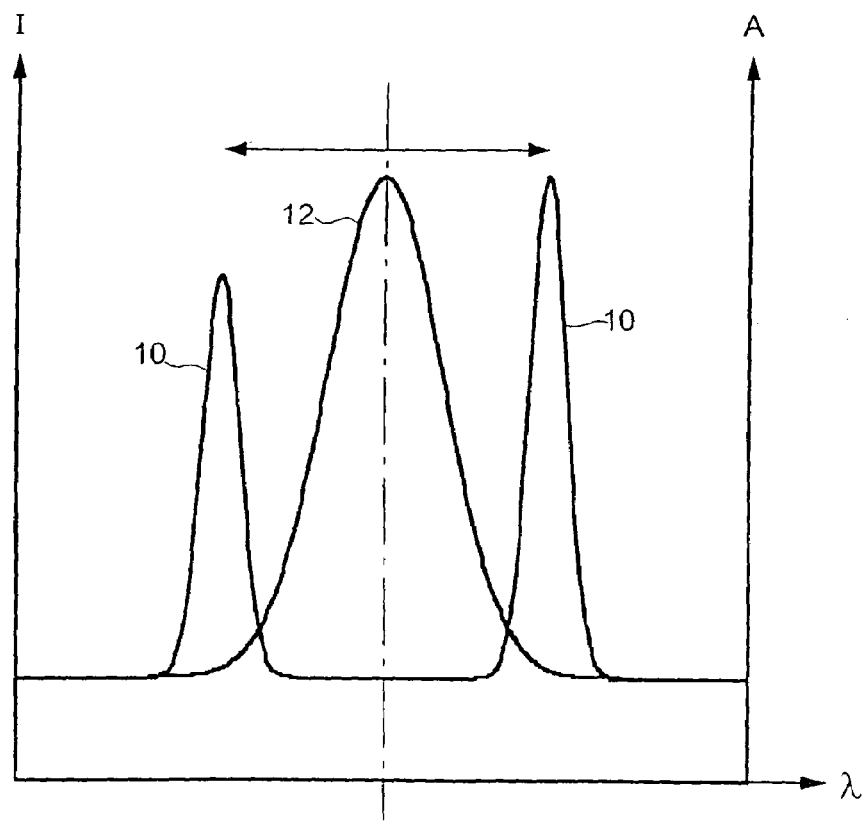
FIG. 2 shows the wavelength modulation of a VCSEL source around a gas absorption line used to detect the concentration of this gas.
Figure 3:
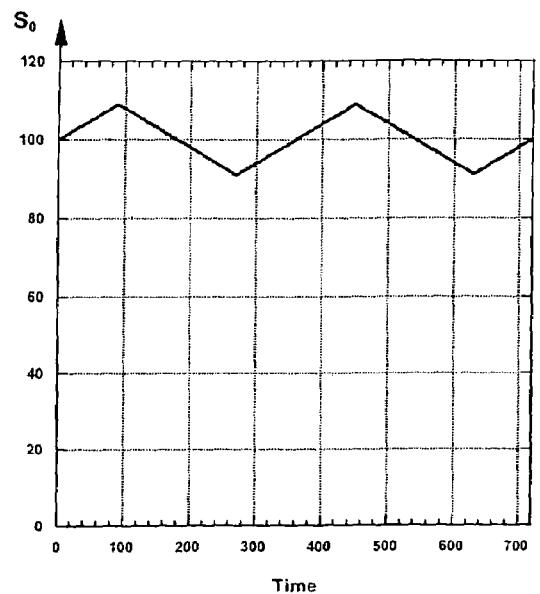
FIG. 3 shows the light intensity modulation of the initial light beam provided by the VCSEL source and resulting from the wavelength modulation of FIG. 2.

As shown in FIG. 2, the VCSEL wavelength λ (center of the light intensity peak 10) is modulated within a small range around a given gas absorption line 12. This wavelength modulation is directly coupled to an amplitude modulation of the initial light intensity, indicated in FIG. 2 by different intensity peak heights. FIG. 3 shows the intensity variation of the initial light signal $S_0$ over time resulting from an alternative scanning around the gas absorption line.

Figure 4:
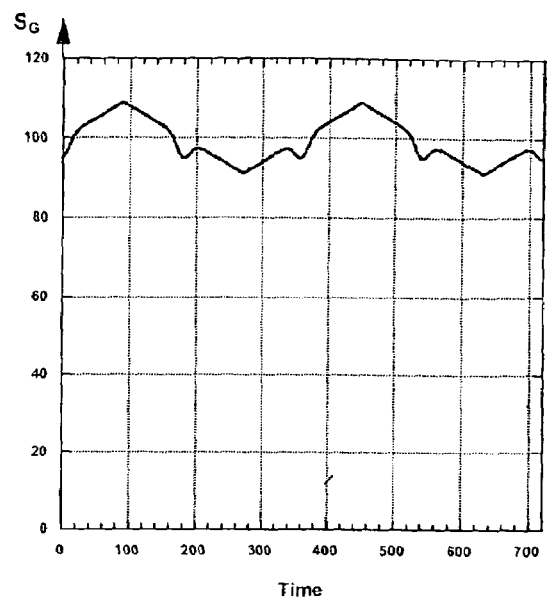
FIG. 4 gives the graph of a resulting light beam having passed through a gas sample.

The intensity variation of the resulting light signal $S_G$ exiting the gas absorption chamber or region 4 is shown in FIG. 4. This signal $S_G$ has therefore two contributions:

The first contribution stems from the fact that the intensity of the VCSEL varies (approximately linearly) with its wavelength. This contribution is independent of the gas absorption and exists even if no gas is present.

The second contribution stems from the gas absorption as the wavelength is scanned across the gas absorption line. This contribution is linearly proportional to the light intensity emitted by the VCSEL and it is a function of the gas concentration in the gas absorption region.

Figure 5:
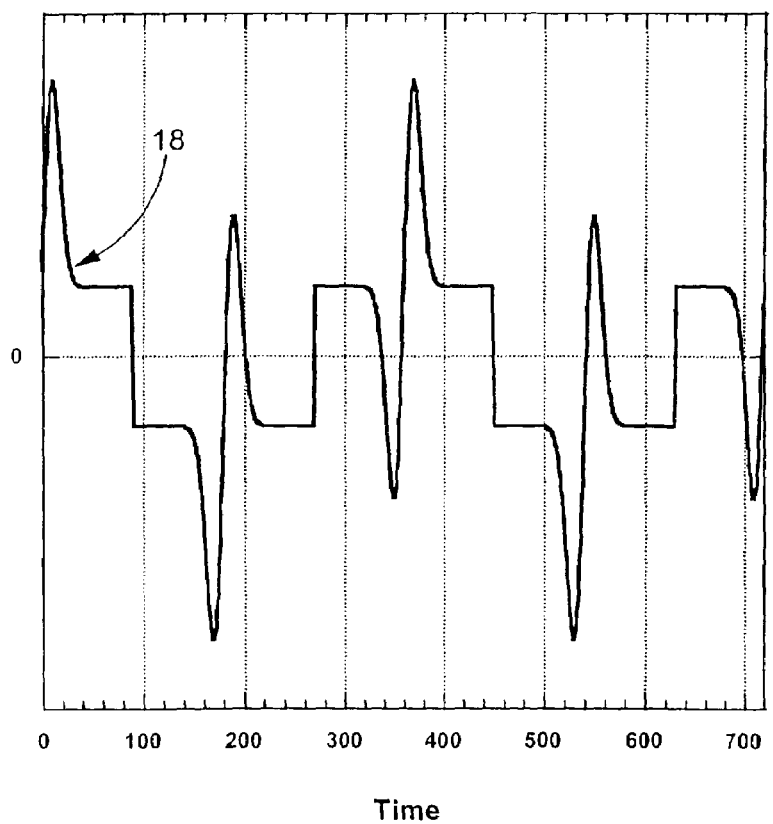
FIG. 5 is a graph of a signal proportional to the time derivate of the signal shown on FIG. 4.

To separate these two contributions, the measurement principle of the present invention first proposes to obtain the time derivate of the resulting light signal $S_G$ and then to process the time derivate signal 18 shown in FIG. 5 with so-called lock-in amplifiers as will be described in more details hereafter.

In a lock-in amplifier, a modulated signal is multiplied with a symmetrical rectangular signal ("modulation reference") which has a well defined phase relation to the modulated signal. The resulting electronic signal is then integrated over a number of modulation periods in order to give a measuring signal at the output of the lock-in amplifier.

Figure 6:
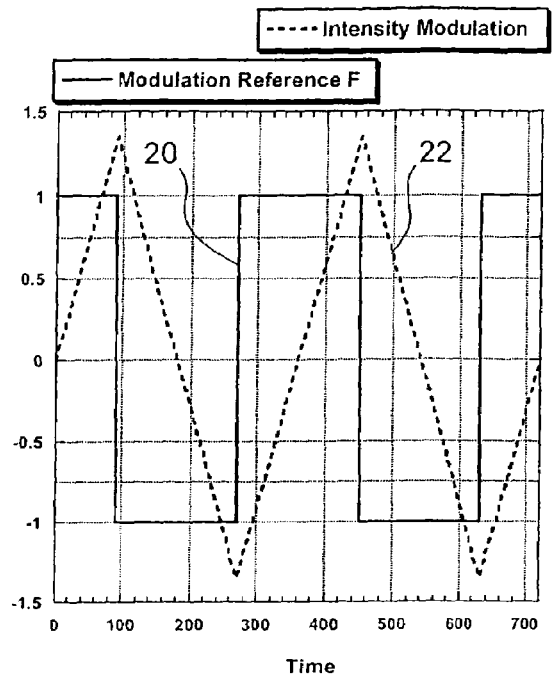
FIGS. 6 and 7 respectively show first and second modulation reference signals at frequencies F and 2F, F being the frequency of the wavelength modulation given on FIG. 2.
Figure 7:
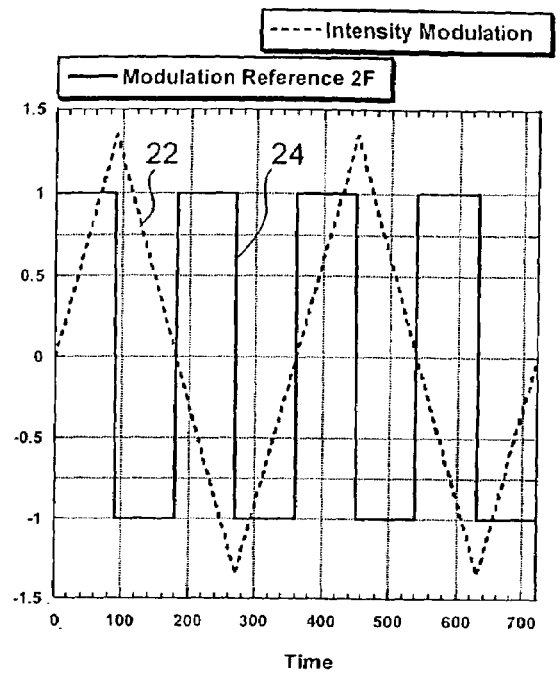

FIG. 6 shows a first modulation reference signal 20 at the Frequency F which corresponds to the Frequency of the scanning by the VCSEL source, that is to the Frequency of the intensity modulation 22 of the initial light signal $S_0$. This FIG. 6 also shows the phase relation between the intensity modulation signal 22 and the first modulation reference 20 generated from this signal 22. FIG. 7 shows a second modulation reference signal 24 at twice said Frequency F. This FIG. 7 also shows the phase relation between the intensity modulation signal 22 and the second modulation reference 24 generated from this signal 22.

According to the invention, the time derivate of the resulting light signal $S_G$ is either directly obtained by the use of a pyroelectric sensor which yields a signal substantially proportional to the change of the light intensity received by this pyroelectric sensor or it is obtained by an electronic derivator in the case that the employed sensor produces a signal $S_D$ substantially proportional to the incident light signal $S_G$ (i.e. photodiode, thermoelement, bolometer).

Figure 8:
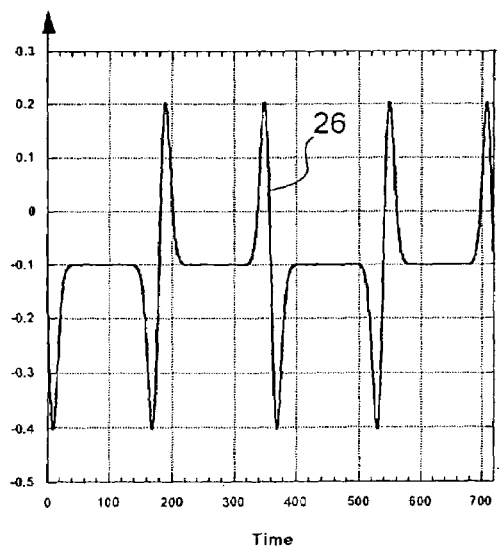
FIG. 8 shows a first resulting signal generated by the multiplication of the signal of FIG. 5 by the first modulation reference of FIG. 6.

FIG. 8 shows the resulting curve 26 of the multiplication of the time derivate intensity signal 18 (FIG. 5) with the first modulation reference signal 20 at the VCSEL modulation frequency F. It is obvious that the subsequently positive and negative contributions from gas absorption cancel out in an time integration of the resulting curve 26, so called F-detection. The result of such a time integration is a first measuring signal $S_{MF}$ that is a function of the modulation of the VCSEL intensity and related to the overall VCSEL intensity, but which is independent of the presence of a gas in the detection region.

Figure 9:
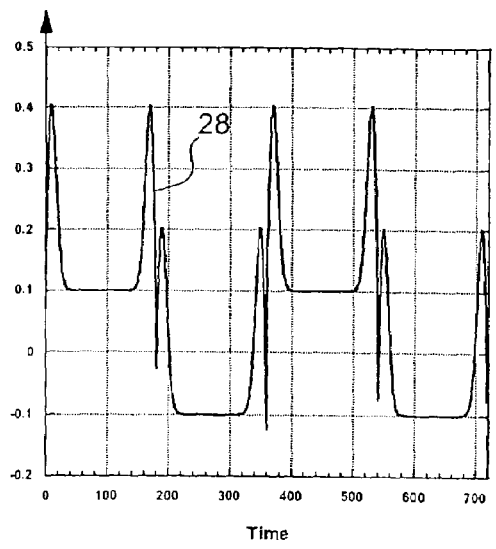
FIG. 9 shows a second resulting signal generated by the multiplication of the signal of FIG. 5 by the second modulation reference of FIG. 7.

FIG. 9 shows the resulting curve 28 of the multiplication of the time derivate intensity signal 18 (FIG. 5) with the second modulation reference signal 24 at twice said frequency F. Here, the contribution from the VCSEL intensity modulation cancel out in a time integration of the resulting curve 28, so called 2F-detection, whereas the individual contributions of the gas absorption will add up. The result of such an integration is a second measuring signal $S_{M2F}$ that is a function of the gas absorption and thus of the gas concentration. Said Integration cancels the contribution which is independent of gas absorption.

The second measuring signal $S_{M2F}$ is in fact substantially proportional to the overall light intensity coming from the VCSEL. By dividing this second measuring signal $S_{M2F}$ by the first measuring signal $S_{MF}$, one obtains a value which is a function of the gas concentration but independent of the light intensity incident onto the detector.

A gas sensor according to the invention, based on a VCSEL and a two-channel lock-in amplifier, provides therefore gas absorption signal and VCSEL intensity reference with one single detector so that the need for a separate physical reference channel as used in conventional NDIR sensors is suppressed. Moreover, the intensity reference value is obtained directly from the light incident on the detector whereas a two-beam NDIR sensor obtains such a reference from a separate beam which may not give information about changes in the measurement beam (i.e. aging of optical components or misalignments due to thermal variations).

The analysis of the measuring signals $S_{MF}$ and $S_{M2F}$ shows that the phase relation between the intensity modulation signal of the VCSEL and the modulation reference signals 20 and 24 as depicted in FIGS. 6 and 7 is critical for the measurement principle. A deviation from this given phase relation will result in contributions of the gas absorption signal ($S_{M2F}$) to the intensity reference signal ($S_{MF}$), and vice versa.

A more extensive analysis of the signals shows that the signal processing described above is not dependent on the shape of the VCSEL AC modulation, i.e. instead of the triangular modulation depicted in FIG. 3, the modulation may as well be sinusoidal, saw tooth or of another shape.

VCSEL sources can be wavelength modulated in a wide frequency range from a few Hz to several MHz. As a consequence, a gas sensor according to the present invention can be built to yield response times from several seconds to several microseconds, depending on the required specification.

Figure 10:
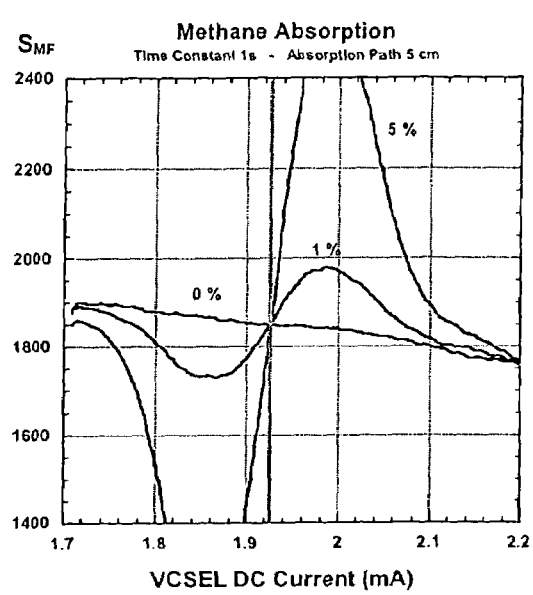
FIGS. 10 and 11 show variations in a first measuring signal and in a second measuring signal provided by a gas detector device of the present invention in function of the central wavelength of the modulation of the VCSEL source relative to an absorption line.
Figure 11:
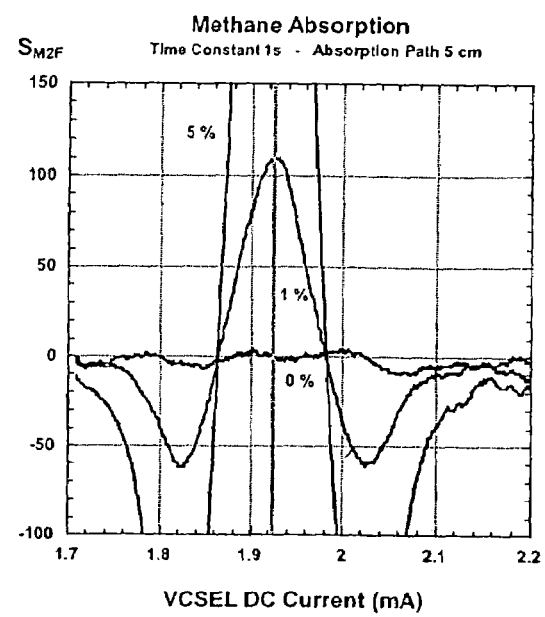

FIGS. 10 and 11 show the influence of the position of the VCSEL central wavelength (which is adjusted by the VCSEL DC current) with respect to the center of gas absorption line on the two measuring signals. The curves were taken by ramping the VCSEL DC current up while applying a small AC modulation corresponding to a wavelength modulation of 0.15 nm. It is evident that the measurement principle as described above only holds if the VCSEL wavelength is exactly centered on the gas absorption line and the AC modulation scans symmetrically across the gas absorption line. A deviation from this center position yields a decreased absorption signal as well as an error in the reference signal. However, the latter decreases with decreasing gas concentration.

Figure 12:
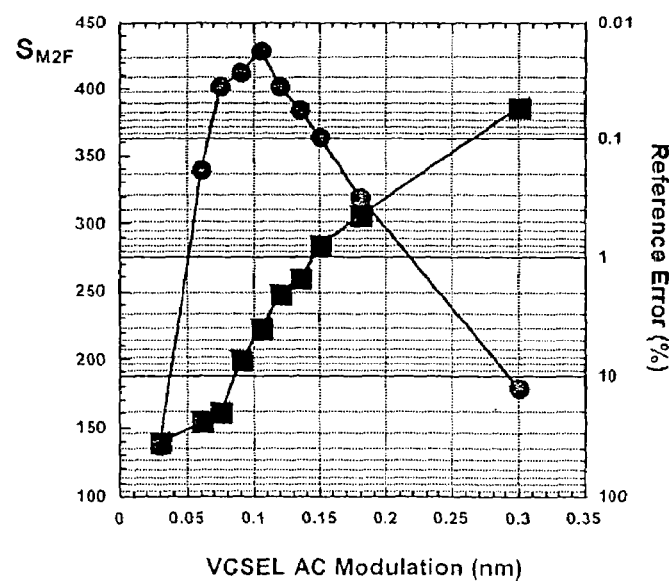
FIG. 12 shows variations in the second measuring signal in function of the amplitude of the VCSEL modulation.

As shown in FIG. 12, the amplitude of the VCSEL AC modulation has an influence on both first and second measuring signals. The signal analysis shows that the gas absorption signal $S_{M2F}$ has a maximum for a modulation amplitude on the order of magnitude of the width of the gas absorption line (0.1–0.15 nm). The error of the intensity reference signal $S_{MF}$ decreases with increasing modulation amplitude. In consequence, the modulation amplitude can be optimised for a given specification of the gas sensor.

Since the wavelength of a VCSEL is a function of ambient temperature, the center wavelength of the VCSEL has to be kept locked onto the exact wavelength of the gas absorption line (see FIGS. 10 and 11). This can be achieved by including a sealed transparent cell in the light path which contains the gas to be detected. On switching on of the gas sensor, the VCSEL DC current is slowly ramped up from a default DC value while scanning with the AC frequency F until the gas absorption line comes to lie within the AC modulation range. From this point on, the gas absorption signal will be non-zero and a feedback loop to the DC current source will keep this signal at its maximum which corresponds to the locking of the VCSEL central wavelength to the gas absorption line center. However, because the wavelength variation of a given VCSEL is limited, it is necessary to keep the VCSEL source approximately at a predefined temperature. In the case of a $CO_2$ detector for ambient air, the sealed cell can be omitted as the natural concentration of $CO_2$ of 350–400 ppm is sufficiently high for the described locking purpose.

The fact that the light emitted by a VCSEL is highly directional allows for a simple design for a multi-gas sensor without further optics. In such a device, several VCSELs (each of a wavelength corresponding to a different gas) are mounted into a laser head whereas the detector is an array of as many light sensors as the laser head contains VCSELs. Mounting is done in a way that the laser beam of each VCSEL aims at a different sensor which yields a very compact multi-gas detection device for two, three or more different gases.

Concerning the laser source, a distributed feedback laser (DFBLaser) can also be selected in the frame of the present invention. VESELS and DFBLasers are preferred laser sources.

Figure 13:
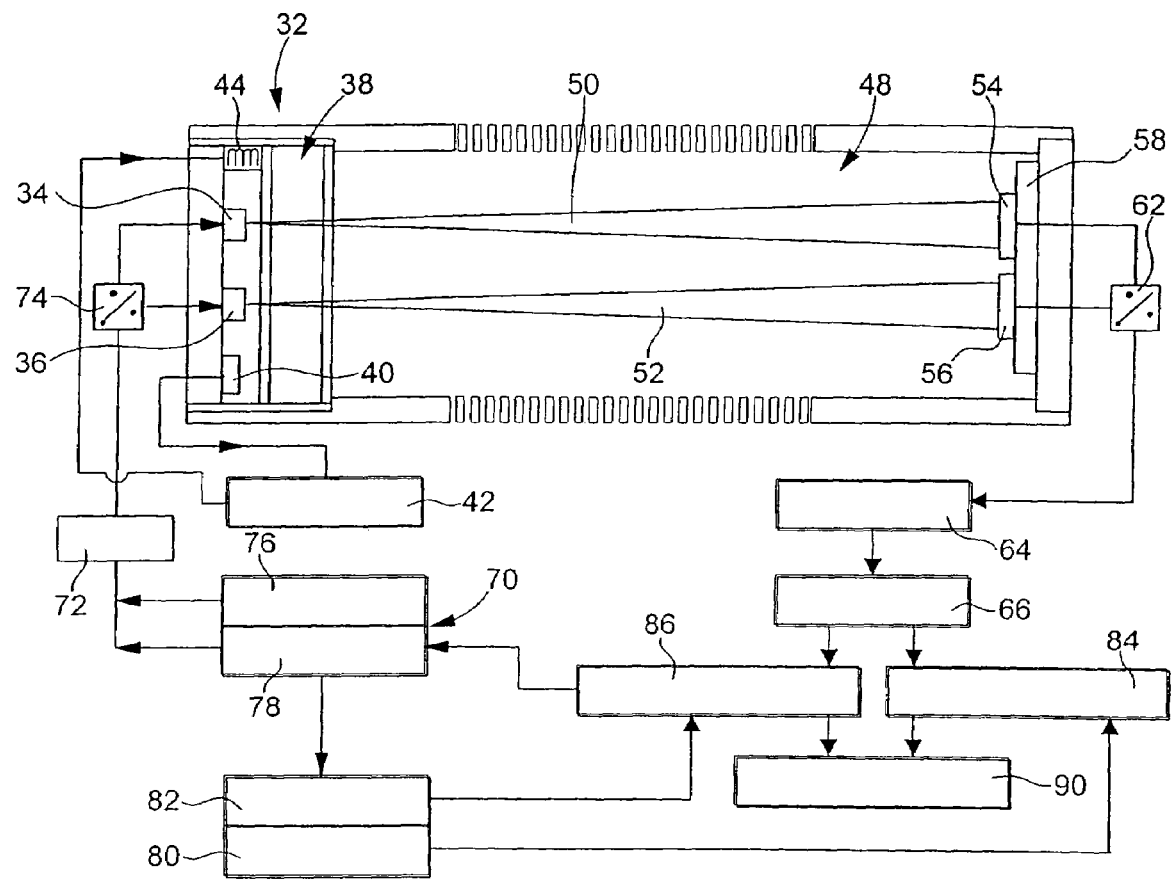
FIG. 13 is a schematic view of a first embodiment of the gas detector device according to the present invention.

FIG. 13 shows a first embodiment of a gas detector device according to the invention. This device comprises a laser light emitting head 32 in which two VCSEL sources 34 and 36 are arranged. Thus, this device forms a detector for two different gases, both sources being respectively chosen for corresponding to selected absorption lines of these two gases. This head 32 further comprises a sealed cell filled with said two different gases for precisely determined the electrical current value to be furnished to each source 34 and 36 so that the central wavelength of the provided light peak corresponds to the center of the absorption line of the respective gas, as explained here-before. Finally the head 32 comprises a temperature sensor 40 electrically connected to power supply means 42 of heating means 44 located in the region where the sources are arranged.

The gas detector device has a sample chamber or gas detection region 48 through which the two laser beams 50 and 52 provided by the two laser sources pass through. The two laser beams are then received by two respective light sensors 54 and 56 arranged on a common base 58. In this first embodiment, the two sensors are of the type providing an electrical detection signal substantially proportional to the incident light signal on the sensor, as a thermoelement or a bolometer or preferably a photodiode. According to the invention, the two sensors 54 and 56 are connected, through an electronic selector 62, to an electronic time derivator 64. This derivator thus provides an electronic signal which is substantially proportional to the time derivate of said incident light signal to preamplifier means 66.

The gas detector device further comprises supply control means 70 connected to electrical supply means 72 which furnish an electrical current to the sources 34 and 36 through an electronic selector 74. The supply control means 70 have a first part 76 for defining a DC current signal and a second part 78 for defining an AC current signal at a given reference frequency F generating an alternative scanning around the gas absorption line as explained before. The processing means of the device also comprise first means 80 for generating a first modulation reference signal at said reference frequency F and second means 82 for generating a second modulation reference signal at twice said reference frequency F. According to the method of the present invention described before, these first and second modulation reference signals are respectively provided to two lock-in amplifiers 84 and 86 in which these reference signals are respectively multiplied with the signal provided by the time derivator 64 to these two lock-in amplifiers through the preamplifier means, and then integrated over several time periods of the first modulation reference signal. The first lock-in amplifier 84 provides a first measuring signal which is independent from the gas absorption as explained before. The second lock-in amplifier 86 provides a second measuring signal which is independent of the modulation of the initial light signal generated by the respective source and relative to the gas absorption and thus to the gas concentration in the region 48.

In a preliminary step, the second measuring signal is used to define the DC current signal by detecting the maximum of this second measuring signal when the DC current level is linearly varied. It is to be noted that this preliminary step can be avoided if the device is equipped with a very precise temperature control for the laser source.

Finally, the second measuring signal is divided by the first measuring signal in an processing unit 90 in which the result of this division is further processed in order to furnish a useful signal or information relative to the presence of a given gas or to its concentration.

Figure 14:
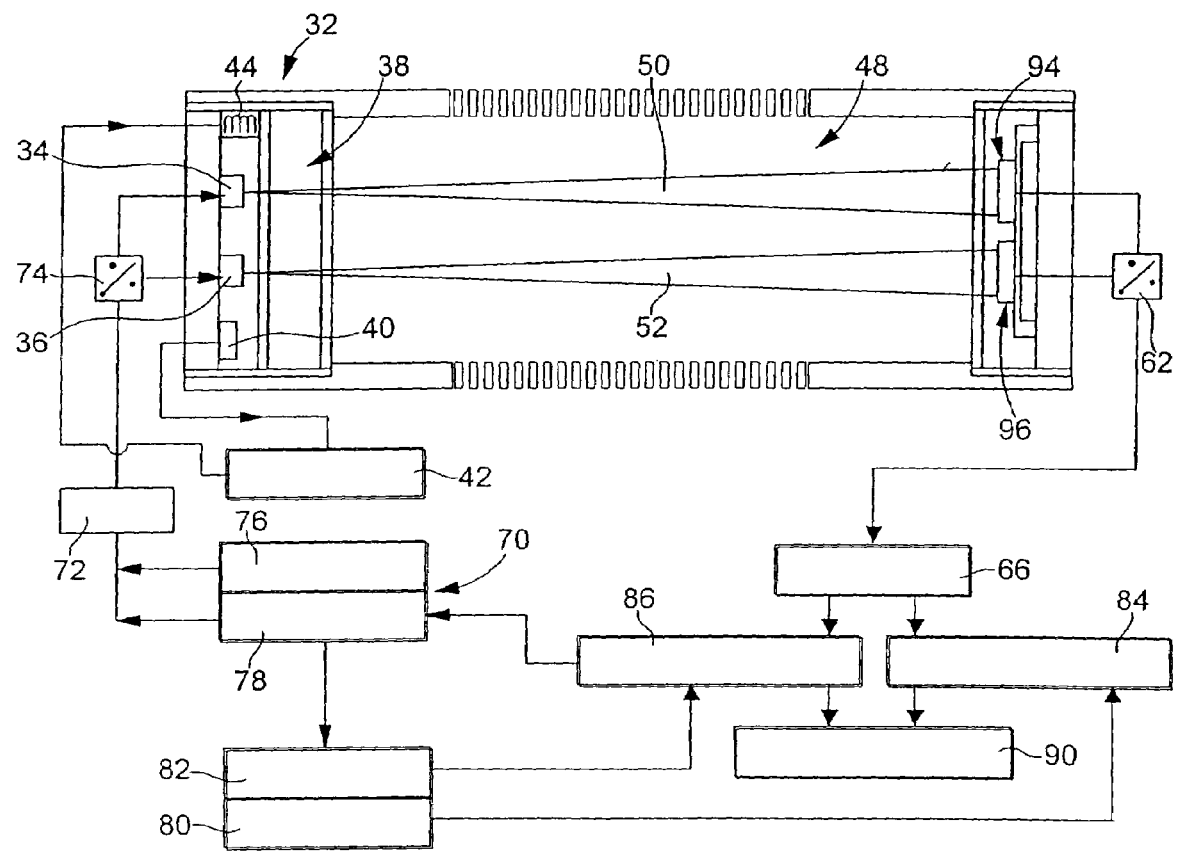
FIG. 14 is a schematic view of a second embodiment of the gas detector device according to the present invention.

FIG. 14 shows a second embodiment of a gas detector device according to the invention. The references already described in the first embodiment will not be described again here. This second embodiment differentiates from the first one in that the two light sensors 94 and 96 are of a specific type and provide directly an electrical detection signal which is substantially proportional to the time derivate of the incident light signal on these sensors. Preferably, the sensors 94 and 96 are pyroelectric sensors. Thus the electronic time derivator is no more needed in this second embodiment. The electrical detection signal is directly provided to the two lock-in amplifiers 84 and 86 through a preamplifier 66.

In a preferred embodiment of the device of the invention, both source and light sensor are located on the same side of the gas detection region, a reflective structure being arranged at the opposite side. Thus, for a given length of the gas detection region, the path of the light through the gas sample is twice as long as in the first and second embodiments shown on FIGS. 13 and 14. Further, the source, the sensor and the electronic elements can be integrated in/on a common substrate, which is very advantageous and cost reducing. The reflective structure can be used for focusing the light beam, especially when its numerical aperture is relatively high.

In another embodiment of the invention for the detection of two gases, the device comprises two laser sources but only a single light sensor, the two generated light beams being oriented in order to be incident on this light sensor. Like in the embodiment of FIGS. 13 and 14, a time multiplexing in the control of both sources allows to measure the concentration of two gases. Thus the two light beams are alternatively directed on the single light sensor.

Finally, if the absorption lines of different gases are sufficiently narrow, it is possible to use only one laser source for detecting these gases.

The gas detector according to different features of the invention has the following advantages:

Suppression of the reference beam which is especially important for multi-gas measurements, No influence of the degrading of optical components or VCSEL intensity, Low power consumption, enabling wireless devices, Low heat dissipation, thus no cooling issues, Temporal resolution down to microseconds, Automatic detection of VCSEL malfunction, Active temperature compensation, Spectral auto-locking, Compact design for multi-gas detector, Low fabrication cost for large series as VCSELs, detector and readout electronics can all be fabricated by batch processing techniques.

The invention claimed is:

1. Gas detection method comprising the following steps of providing an initial light signal, by a wavelength modulated laser source, said initial light signal is wavelength modulated at a first frequency symmetrically around an absorption line of a gas the concentration or presence of which is to be determined;

passing said initial light signal having intensity variations over the time resulting from an alternative scanning around said gas absorption line through a gas detection region intended for receiving at least one of said gases;

receiving a resulting light signal exciting said gas detection region, by detection means, said resulting light signal comprises changes in the intensity of the initial light signal due to the gas concentration in the detection region;

generating a detection signal by said detection means being substantially proportional to the time derivate of said resulting light signal;

generating a first measuring signal from said detection signal, which is a function of intensity of said initial light signal;

generating a second measuring signal from said detection signal, which is a function of the gas absorption and substantially independent of an intensity modulation of said initial light signal at said first frequency $(F)$;

providing a final measuring signal being independent from the intensity of light incident onto the detection means by dividing said second measuring signal by said first measuring signal and thereby providing a signal relative to the presence or the concentration of a given gas.

2. Gas detection method according to claim 1, wherein said first measuring signal is generated by multiplying said detection signal with a first modulation reference Signal at the first frequency and then integrated over time, and said second measuring signal is generated by multiplying said detection signal with a second modulation reference signal at twice of that frequency and then integrated over time, whereby the first modulation reference signal and the second modulation reference signal are exactly defined in phase with the intensity variations of said initial light signal.

3. A gas detector device comprising:

a wavelength modulated laser source providing an initial light signal;

a detection region intended for receiving at least one of a gas the concentration or presence of which is to be determined;

supply control means for wavelength modulating said initial light signal at a first frequency symmetrically around an absorption line of one of said gases and providing said initial light signal having intensity variation over the time;

a light sensor respectively arranged at the periphery of said detection region, said sensor is intended for receiving a resulting light signal comprising changes in the intensity of the initial light signal having passed through said detection region and providing a detection signal proportional to the light intensity variation of said resulting light signal;

processing means for providing from said detection signal a signal relative to the presence or the concentration of a given gas in said detection region; wherein said light sensor or said processing means comprise means for providing a detection signal substantially proportional to the time derivate of said resulting light signal; and said processing means further comprise first means for generating a first modulation reference signal at said first frequency and second means for generating a second modulation reference signal at twice said first frequency, first means for multiplying said first modulation reference signal with said detection signal and then integrating over time the resulting signal in order to provide a first measuring signal which is a function of the intensity of said initial light signal and substantially independent of the concentration of said gas, second means for multiplying said second modulation reference signal with said said detection signal and then integrating over time in order to provide a second measuring signal which is a function of the gas absorption and substantially independent of an intensity modulation of said initial light signal at said first frequency, a processing unit for dividing said second measuring signal by the first measuring signal and providing a signal relative to the presence of a given gas or to its concentration.

4. The gas detector device according claim 3, wherein supply control means comprise a first part for defining a DC current signal and a second part defining an AC current signal at said given reference frequency for generating an alternative scanning of light intensity of said initial light signal around said gas absorption line.

* * * * *